(12) United States Patent
Sieben et al.

(10) Patent No.: US 6,245,057 B1
(45) Date of Patent: Jun. 12, 2001

(54) DEVICE FOR TREATING MALIGNANT, TUMOROUS TISSUE AREAS

(75) Inventors: Ulrich Sieben, Reute; Bernhard Wolf, Stegen, both of (DE)

(73) Assignee: Micronas Intermetall GmbH, Freiburg (DE)

( * ) Notice: Subject to any disclaimer, the term of this patent is extended or adjusted under 35 U.S.C. 154(b) by 0 days.

(21) Appl. No.: 09/425,598

(22) Filed: Oct. 22, 1999

Related U.S. Application Data

(63) Continuation of application No. PCT/EP98/02133, filed on Apr. 11, 1998.

(30) Foreign Application Priority Data

Apr. 23, 1997 (DE) .............................................. 197 17 023

(51) Int. Cl.[7] .................................................. A61K 9/22
(52) U.S. Cl. ........................................ 604/891.1; 424/422
(58) Field of Search ........................... 604/65, 66, 890.1, 604/891.1, 20, 503; 424/422

(56) References Cited

U.S. PATENT DOCUMENTS

| | | |
|---|---|---|
| 4,003,379 | 1/1977 | Ellinwood, Jr. . |
| 4,425,117 | 1/1984 | Hugemann et al. . |
| 4,531,524 | 7/1985 | Mioduski . |
| 4,793,825 * | 12/1988 | Benjamin et al. ................ 604/891.1 |
| 5,209,717 | 5/1993 | Schmoll et al. . |
| 5,279,607 * | 1/1994 | Schentag et al. . |
| 5,301,688 | 4/1994 | Stephen et al. . |
| 5,505,700 | 4/1996 | Leone . |
| 5,820,548 * | 10/1998 | Sieben et al. . |
| 6,033,916 * | 3/2000 | Sieben et al. . |

FOREIGN PATENT DOCUMENTS

| | | |
|---|---|---|
| 36 34 864 C2 | 11/1995 | (DE) . |
| 196 01 487 A1 | 7/1997 | (DE) . |
| 0 510 857 A1 | 10/1992 | (EP) . |
| WO 94/01165 | 1/1994 | (WO) . |
| WO 94/05361 | 3/1994 | (WO) . |

OTHER PUBLICATIONS

James B. Brinton, "System to Detect and Treat Cancer, Using Microwaves For Both Tasks", *Electronics*, No. 26 Dec. 20, 1979.

Thomas Severin, et al., "pH–Dependent LAK Cell Cytotoxicity", *Tumor Biol* 15:304–310 (1994).

B. Wolf, et al., "The Physiocontrol–Microsystem: Development and Characterization of Cellular Bisensors", *SENSOR 95 Kongressband*, pp. 869–871 (1995).

* cited by examiner

Primary Examiner—Anhtuan T. Nguyen
Assistant Examiner—Jeremy Thissell
(74) Attorney, Agent, or Firm—Akin, Gump, Strauss, Hauer & Feld, L.L.P.

(57) ABSTRACT

A device (1) functions for treating malignant, tumorous tissue areas. The device has at least one measuring sensor for determining chemical or physical signal patterns in the immediate vicinity of the tumor cells or similar tissue part, a control unit and at least one treatment assembly, which has as an active agent release element for chemically influencing and/or treatment electrodes for physically influencing the tumorous tissue area to be treated. The sensor(s), the active agent release element, and the treatment electrodes are connected to the control unit for a physical and/or chemical treatment of the tumorous tissue area, controlled as a function of the measured values of the tumor cells. The device is constructed in the form of a swallowable capsule or dragée, and a sensor is provided for detecting release parameters. The control unit is designed with a threshold value switch for activating the active agent release element and/or the electrodes when a predetermined target value is exceeded.

21 Claims, 2 Drawing Sheets

DEVICE FOR TREATING MALIGNANT, TUMOROUS TISSUE AREAS

CROSS REFERENCE TO RELATED APPLICATION

This application is a continuation of International Application PCT/EP98/02133, Filed Apr. 11, 1998, the disclosure of which is incorporated herein by reference.

BACKGROUND OF THE INVENTION

The invention relates to a device for treating malignant, tumorous tissue areas, the device having at least one measuring sensor for determining chemical or physical signal patterns in the immediate vicinity of the tumorous tissue area, and having a control unit as well as at least one treatment assembly. The treatment assembly has at least one active agent supply container, a dosing element with dosing control, an active agent release element for chemical influencing and/or treatment electrodes for physically influencing the tumorous tissue area to be treated. The sensor(s), the active agent release element and the treatment electrodes are connected to the control unit for a physical and/or chemical treatment of the tumorous tissue area, the treatment being controlled as a function of the measured values of the tumor cells, with constant follow-up dosing of the active agent to be applied.

In cancer therapy, for example, it is already known to use chemotherapeutics, which should damage the pathogenic organ parts but, to the greatest extent possible, not the remaining organism. However, the systemic and regional dosing of chemotherapeutics is problematic since, on the one hand, a high effectiveness against a tumor, for example, is desired by using an appropriate active agent concentration, but, on the other hand, there is the danger of damage to the healthy tissue through non-specific absorption.

From the publication Brinton. J. B., "System to Detect and Treat Cancer Using Microwaves for Both Tasks," Electronics, 26;42 (1979), a system for detecting and treating cancer is known. There, tumors are localized using microwaves and then destroyed. In particular, using a radiometer, the slightly raised temperature in the area of a tumor is used to detect the tumor. This involves a one-time, short-term overheating and destruction of the tumor. A treatment of this type can, of course, be performed for very small tumors, but for larger tumor areas this method cannot be used.

From German patent DE 196 01 487 a device is known for use in directly or operationally accessible areas. For areas which cannot be opened by operation, however, a device of this type cannot be used.

SUMMARY OF THE INVENTION

An object of the present invention is to create a device with which a target-oriented release of medication is possible, in which the burden and damage to the non-affected areas of the body are at least largely reduced.

To achieve this object, it is proposed that the device be constructed in the form of a capsule or dragee to be swallowed and that it have a sheath which at least covers the sensor(s). The sheath can be soluble (removable) at least over a certain area under the influence of bodily fluid. A sensor for detecting release parameters and the control unit are constructed with a threshold value switch for activating the active agent release element and/or the electrodes when exceeding a predetermined or predeterminable target value. For release of active agent within the active agent supply container, at least one heat resistor is provided for heating up and for release of active agent.

From PCT publication WO-A-94/01165 a capsule-shaped device is indeed known for release of medication. This device makes possible a controlled release of medication using a preprogrammed microprocessor. The beginning of the medication release is triggered by the contact of the capsule with gastric acid, for example. However, the medication release then proceeds according to a program that is prespecified prior to swallowing of the capsule. A change in the dosing in adaptation to the actual conditions is thus no longer possible.

Using the device according to the invention, in contrast, a target-oriented medication release can occur after an oral administration. Here, after the device is located in the area of a tumor or the like, which is to be treated, a medically active agent is applied to induce a chemical effect, and at the same time, in the immediate vicinity of the treatment location a constant monitoring during treatment is performed using the sensor(s). Based on the measured values, the dosing can be adapted according to the target value specifications of the control unit. Thus, an automatically operating control loop is formed, by which a constant follow-up dosing can be performed with the active agent to be applied.

In this control process, the active agent release is thus controlled during a chemical treatment and/or the intensity is controlled during the physical treatment as a function of a measured value. Thus, not only is a treatment triggered, but the treatment also proceeds by measurement of release parameters, for example the pH-value. This also means that when a threshold value is not reached, the treatment stops.

Thus, a target-oriented medication release and consequently a treatment in a selected manner is possible, since after the capsule is swallowed, the removal of the protective sheath occurs first, so that then the sensor(s) are exposed and are in a position to record specified release parameters. If the capsules in this activated condition comes into the area of malignant, tumorous tissue, then this is recognized using the pH-value, for example, and depending on the deviation of the pH-value from the standard pH-value in this surrounding area of the body, a chemical and/or physical treatment is performed in a controlled manner. When the capsule is transported further and emerges from the area of the tumorous tissue to be treated, the treatment is reduced and finally stopped.

The active agent release is accomplished by heating the active agent, wherein the active agent supply container preferably has at least one capillary tube for active agent release. This active agent release by heating the active agent can be performed in an especially simple manner, and requires almost no additional space and makes possible a quick and exact dosing. By the thermal effect of the heating resistor, the liquid expands and is released from the supply container in the direction of the support and contact area. The release of the active agent via the support and contact area can also be accomplished both iontophoretically as well as thermally via a suitable thermal micropump or a thermal valve.

Using the device according to the invention, a target-oriented medication release can also be carried out by oral ingestion for stomach and intestinal diseases, for example by a targeted alkali release or the release of another active agent.

Release parameters for the start of the treatment can be the pH-value, which is measured constantly, for example, and upon deviation from a prespecified value triggers the treatment, in particular by the release of active agent. Aside from the pH-value measurement mentioned as an example, a calcium measurement, an impedance measurement the like can be performed.

The device can be placed within the digestive tract without surgical intervention at prespecified locations, and a targeted treatment can be carried out there, or medications can be released in a targeted manner via the digestive tract.

With the sheath the capsule or the dragee is inactive prior to being swallowed, and it first becomes active when the sheath is dissolved. The sheath also practically forms a protective sheath, which is advantageous for longer storage prior to the treatment application.

For an exact positioning or activation of the device in a prespecified treatment area within the digestive tract, the sheath can be triggered especially in a time-dependent and/or substance-dependent manner by the bodily fluid. By various sheath materials and also by their wall thicknesses, the position of the device within the digestive tract can be prespecified to a sufficiently exact extent for its activation and also the point in time of activation. In the course of the digestive tract different digestive juices act on the sheath, so that by the targeted selection of the sheath substance, it can be determined under the influence of which digestive juice the activation of the device should occur.

Even the duration of the activation operation, i.e., the time to dissolution or detachment of the sheath, can be prespecified by the sheath material and its thickness.

There is also the possibility that the electrodes covered by the sheath, the release point and the like, can be exposed one after the other corresponding to the prespecified treatment course.

One embodiment of the invention provides that at least for increasing the dwell time of the capsule or the dragee stays at the treatment location, it has a sheath with a filling material or foaming system, in particular on an enzymatic basis, which is designed for an immunobiochemical and/or immuno-enzymatic reaction upon reaching the area of the inflammation or tumor.

By the corresponding reaction the filling material of the capsule is caused to hook up at the affected position, and possibly causes a foaming or swelling by a chemical reaction, and thus an increase in volume.

In this way, the dwell time at the treatment location can at least be prolonged since an "anchoring" occurs at the treatment location. The foaming or swelling material preferably has certain adhesive properties, which also contribute to the increase of the dwell time.

In order also to be able to operate self-sufficiently over a longer time period within the body, the device can have electrodes on the outside for galvanic current generation upon contact with bodily fluid.

Carrying along a battery to generate current is thus not necessary, so that corresponding space can be saved or is available for other devices. Although the battery-less embodiment is preferred, one can be provided in special cases, optionally also as a buffer battery in connection with electrodes for generating current upon contact with bodily fluid or a charging coil.

In order to monitor the treatment area, at least one sensor is provided for determining the acidification or another parameter in the treatment area, since for example, changes of the pH-value allow conclusions to be made about the metabolic activities of the tumor cells and thus corresponding treatment adaptations can be carried out. This is based upon the discovery that growth and spreading of tumors must be considered to be a process of cellular self-organization, which apart from changes in the cellular signal processing system, is essentially controlled by the micro-environment of the tumor. In this way, the pH-value of the micro-environment of the tumor can play a central key role.

If, for example, a pH-target value of 7.4 is prespecified, then a controlled dosing of the medically active agent is performed by the control unit, based on the measurement of the present pH-value as an actual value, until the target value, pH 7.4 in the example, is reached. The medically active agent can be an active agent for the neutralization of the pH-gradient. Furthermore, an active agent (antagonist) can be considered for blocking the proton pump to the cell membranes of the tumor cells or an active agent can be considered for blocking the molecular biological agents (for example, antigenic-products). Instead or in combination with the chemical influence of the tumorous tissue, a physical influence can also be made. This can be done using iontophoresis by electric and/or electromagnetic fields via electrodes on the device. A direct current or an alternating current can be applied at the electrodes.

Also, in this process, the change of the field as a function of the respective measured value can be performed, so that also in this regard a control loop and thus a targeted treatment with "feedback" is available.

As a sensor for determining the acidification in the immediate vicinity of the tumor cells, a pH-sensor based on a semiconductor can be provided or a pH-sensor based on a conductance and impedance measurement, wherein with a pH-sensor based on a semiconductor, preferably at least one ion-selective field effect transistor (IS-FET) is provided.

Using a pH-sensor based on a semiconductor, a high measurement accuracy can be achieved, and a sensor (optionally an immunosensor) based on a conductance and impedance measurement can be applied more easily in a problem-specific manner in certain applications (liver, stomach).

Optionally, in addition to at least one pH-sensor, at least one additional sensor, in particular an ion or molecular sensor is provided.

With these additional sensors, aside from the pH-value changes, additional therapy-relevant changes can also be detected in the micro-environment of a tumor, and from these additional measurement data corresponding measures can be taken when applying the medically active agent.

Expediently, the active agent release element preferably has at least one porous membrane and one active agent supply to this membrane, wherein at the active agent supply a dosing element is located, which is connected to a dosing control. The membrane is optionally chemically modifiable in such a way that it preferably adheres at the location to be treated. Here, the sensor(s) and the optionally-provided, porous membrane thus form a support and contact area for the tissue area to be treated. At this support and contact area for the tissue area to be treated, at least two electrodes can be provided for iontophoretic purposes, which are connected via electrical lines to a voltage source. A regionally limited and dosed supply of active agent is thereby possible.

One embodiment of the invention provides that the functional unit has at least one active agent supply container, one or more dosing elements having dosing control and connected to the porous membrane or the like, as well as at least one pH-sensor.

On the other hand, the possibility exists for a physical influencing, that the functional unit has at least one pH-sensor, at least two electrodes for iontophoretic purposes, a voltage source and a control unit.

If necessary, the functional unit can have devices both for a chemical as well as for a physical treatment or influencing. A device of this type can stay inside the digestive tract for a predetermined treatment period as a complete, functionally efficient unit.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 3:
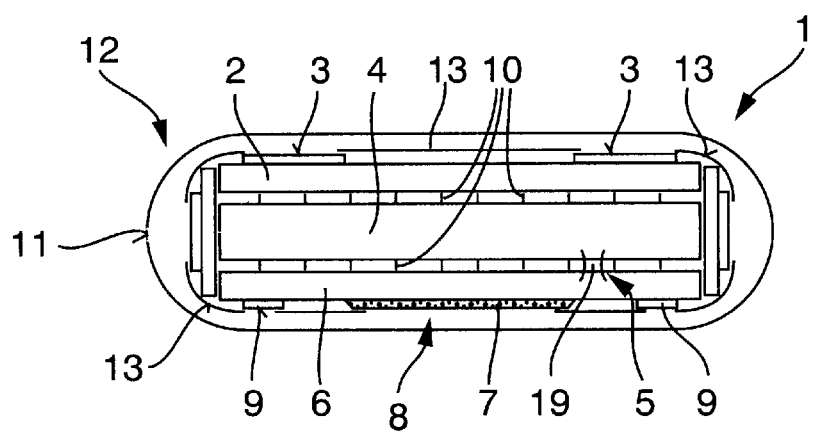

A device 1 shown in FIG. 3 functions for the application of medically active agent in the area of living cell tissue. This can involve, in particular, a tumor to be treated which is located inside the digestive tract. The device 1 is constructed as a capsule that can be swallowed and has accordingly small dimensions with a length of, for example, 20 mm and a diameter or a thickness of several millimeters, for example 5 mm. The mechanical deposition and positioning of the device can be supported both in the stomach as well as in the intestinal area, optionally by an endoscopic technique.

As can be recognized well in FIG. 3, the device 1 comprises essentially three sandwich-type assembly groups arranged on top of each other and connected to each other. On one outer side, a control chip 2 is located, which contains a control unit, by which the chemical and/or physical treatment is controlled as a function of supplied measurement data. On the outer side of this control chip, electrodes 3 are located, which function for galvanic current generation upon contact with bodily fluid.

A container 4 for receiving an active agent is connected to the control chip 2, and the container is connected via a connection channel 5 to an active agent release element 6. This element 6 has a release window 8 which is preferably formed by a porous membrane 7. Next to the release window 8, sensors 9 are located, of which at least one is a pH sensor, by which the pH-value of the area to be treated can be monitored.

The assembly groups 2, 4 and 6 can be constructed as structural components preferably having approximately equal surface areas, which have contact pads 10 on the sides facing each other, by which the assembly groups can be connected to each other preferably using flip-chip-technology.

The unit consisting of the individual structural groups has a sheath 11, which can be dissolved by the bodily fluid in a time dependent and/or material dependent manner. The material composition of this sheath 11 is provided as a function of where the device 1 should be activated within the digestive tract. A coordination to the different bodily fluids acting within the digestive tract is thereby provided.

A sheath can be provided made of different materials, which is made up differently in the area of the electrodes 3 than in the area opposite thereto, where the release window and the sensors are located. For example, it can be provided that after swallowing the device 1, the sheath 11 is at first dissolved at the electrodes 3 in order to generate current, so that the device is then ready to function. If the sheath is then further dissolved in the area of the release window 8 and the sensors 9, then the treatment begins, for example, through the targeted release of active agent at the release window 8.

Aside from the sheath 11, the capsule 12 has an inner protective sheath 13, which has corresponding interruptions in the area of the parts acting to the outside, i.e., electrodes, sensors, release windows.

Figure 1:
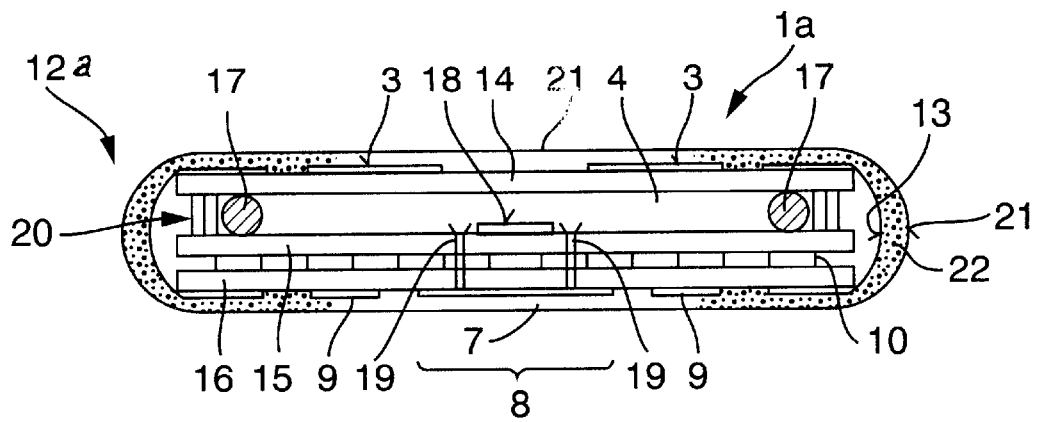
FIGS. 1 to 3 are schematic diagrams of a device according to the invention in different embodiments having three sandwich-type assembly groups arranged above one another.

FIG. 1 shows another embodiment of a device 1a, which is likewise made as a capsule 12a. Even for this embodiment, a three-layer construction is provided using the three chips 14, 15, 16. Between the chip 14 arranged on the outside and the chip 15 adjacent to it, a suitably measured distance is provided in order to form the active agent supply container 4, and a surrounding sealing ring 17 functions as a spacer between these two chips 14 and 15.

Inside the cavern-shaped container 4, at least one heating resistor 18 is provided in order to heat up the active agent located in the container 4. Next to the heating resistor 18 the container 4 in this embodiment has two capillary tubes 19 with a connection connecting them to the release window 8, formed in particular by a porous membrane 7. Upon heating the active agent liquid in the container 4 by the heating resistor 18, the liquid expands and is released via the capillary tubes 19 to the membrane 7.

The sealing ring 17 is arranged on the outer edge of the chips 14 and 15 spaced apart, so that on the outside there is still sufficient space to make an electrical connection between the two chips 14, 15, for example a wire bond, via connection contacts 20. The chips 15 and 16 have contact pads 10 and are connected to each other especially using Flip-Chip-Technology.

The capsule 12a shown in FIG. 1 has a sheath 21 with a filling material or foaming system 21, indicated by dots, in particular based on enzymes. This sheath having or made of suitable material reacts in an immunobiochemical or immunoenzymatic manner when an inflammation area or tumorous area is reached. The capsule 12a can thereby be affixed at the treatment site or at least its dwell time is increased there. By the foaming with corresponding volume enlargement, whereby even an occasional fixed attachment can occur in the treatment area, the continued transport of the capsule 12 within the digestive tract is at least impeded, so that a sufficiently long treatment time is available.

Figure 2:
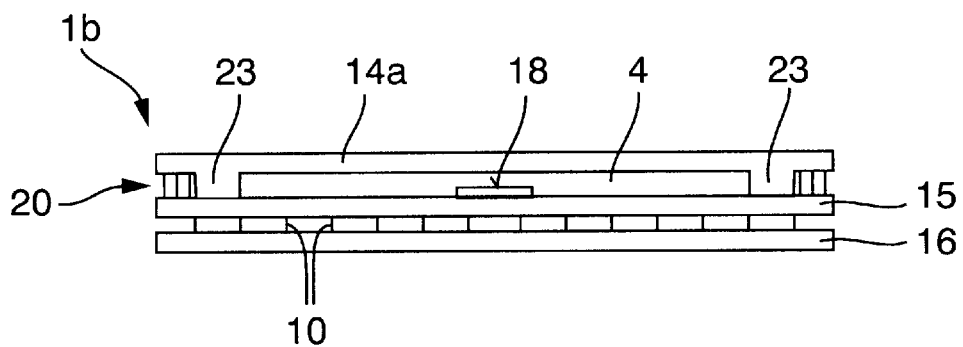

FIG. 2 shows a device 1b principally constructed in a comparable manner with FIG. 1, which likewise has three chips 14a, 15 and 16 layered on top of each other. The chip 14a here has on its side facing the chip 15 a ring wall 23, constructed particularly by etching, as a spacer and to form the active agent supply container 4 between these two chips 14a and 15. The face side of this ring wall is sealingly connected with the chip 15 lying adjacent to it, which is preferably achieved by eutectic bonding. In addition, the construction of the device 1b can correspond to the device 1a shown in FIG. 1.

Figure 4:
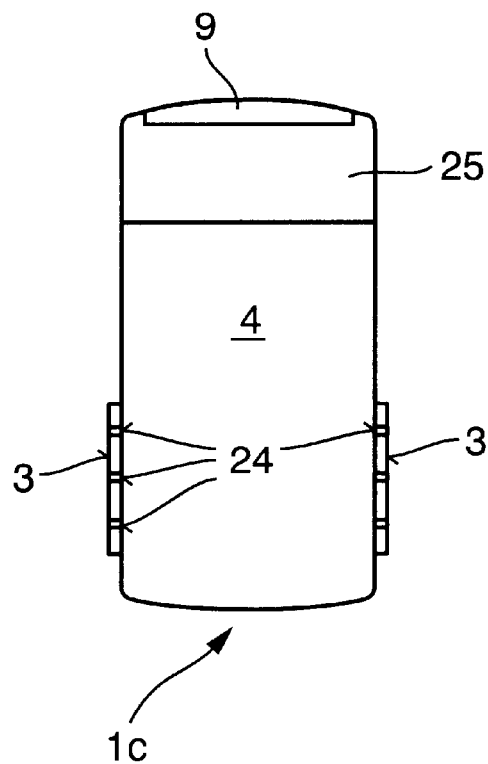
FIG. 4 is a schematic side view of another embodiment of a device according to the invention.

FIG. 4 shows another modified embodiment of a device 1c, which is likewise constructed in a capsule form. The arrangement of the individual assembly groups, however, deviates from the other embodiments. The device 1c likewise has an active agent supply container 4, which has release openings 24 in the area of reference electrodes 3. On one head end of the capsule an electronic part is located having the control device for the physical and/or chemical treatment and the processing of the measured values coming from the sensor(s). The sensor(s) 9 is(are) located on an outer end face of the capsule near the electronic part 25.

Figure 5:
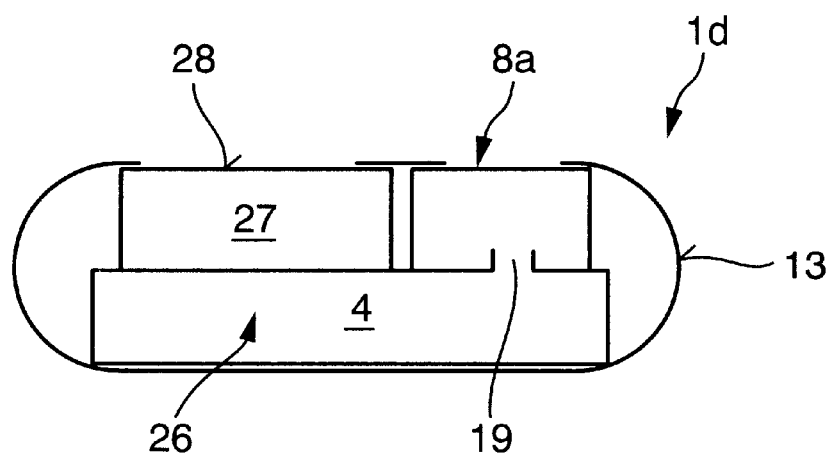
FIG. 5 is a schematic side view of a further modified embodiment of a device according to the invention.

A further modified embodiment is shown in FIG. 5. By 26 is indicated a carrier part, preferably constructed as a chip, in which the active agent supply container 4 is located. In an embodiment as a chip a cavern can be etched into it as a supply container 4 as well as a capillary channel 19. The capillary channel 19 leads to a release window 8a, through which the active agent is released to the outside. The release window 8a with control valve and dosing control can be constructed as a separate chip.

The third function block 27 is also preferably constructed as a chip and contains the control electronics and, on its outer side 28, sensors and optionally also electrodes for current generation. By 13 is designated a protective sheath, which is left open in the area of the release window 8a and the outer side 28.

As indicated in FIGS. 4 and 5, the devices 1c and 1d made as swallowable capsules can be used without a sheath 21 that dissolves under the influence of bodily fluid (compare FIGS. 1 and 3). The activation of the active agent release element and/or the electrodes is accomplished herein as a function of constantly measured release parameters, for example the pH-value. Also, a measurement can be made on an enzymatic basis. If appropriate release parameters are present, then the activation of the active agent release and/or electrodes induced.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A device (1, 1a, 1b, 1c, 1d) for treating malignant, tumorous tissue areas, comprising at least one measuring sensor (9) for determining chemical or physical signal patterns in an immediate vicinity of a tumorous tissue area, a control unit, and at least one treatment assembly having at least one active agent supply container (4), a dosing element with dosing control, and an active agent release element (6) for chemically influencing and/or treatment electrodes for physically influencing the tumorous tissue area to be treated, wherein the sensor(s)(9), the active agent release element(6) and/or the treatment electrodes (3) are connected to the control unit for controlling a physical and/or chemical treatment of the tumorous tissue area as a function of measured values of the tumor cells with continuous follow-up dosing of the active agent to be applied, wherein the device is constructed in a form of a swallowable capsule or a dragée and has a sheath (11) which at least covers the sensor(s)(9), the sheath being removable at least over a certain area under the influence of bodily fluid, wherein the control unit and a sensor for detecting release parameters are designed with a threshold value switch for activating the active agent release element and/or the electrodes when a predetermined target value is exceeded, and wherein at least one heat resistor (18) is provided within the active agent supply container (4) for heating up and release of the active agent.

2. The device according to claim 1, wherein at least for increasing the dwell time of the capsule or the dragée at a treatment location, the device has a sheath (21) with a filling material or foaming system (22), optionally on an enzymatic basis, which is designed for an immunobiochemical and/or immuno-enzymatic reaction upon reaching an area of inflammation or tumor.

3. The device according to claim 2, wherein besides the sensor(s)(9), a release position of the active agent release element(6), and optionally the treatment electrodes are covered by the sheath (11) in a starting condition.

4. The device according to claim 1, wherein the sheath (11) is dissolvable by the bodily fluid as a function of time and/or material.

5. The device according to claim 1, wherein the electrodes (3) include an outer side electrode having galvanic current generation upon contact with the bodily fluid.

6. The device according to claim 1, wherein the control unit, the treatment assembly, the active agent release element are connected to each other in a sandwich structure and form a complete functional unit.

7. The device according to claim 1, wherein individual structural groups are essentially constructed as chips and are connected to each other using flip-chip-Technology.

8. The device according to claim 1, wherein the active agent release element has at least one porous, structured membrane (7) and one active agent supply for the membrane, wherein the dosing element is located at the active agent supply.

9. The device according to claim 1, wherein the device has at least one pH-sensor (9) and optionally at least two electrodes for iontophoretic purposes, a voltage supply and a control unit.

10. The device according to claim 1, wherein the sensor (s)(9) and the active agent release element in a form of a porous membrane (7) function as a support and contact surface for the area of tissue to be treated.

11. The device according to claim 10, wherein the sensor (s)(9) are arranged in a vicinity of the membrane (7).

12. The device according to claim 10, wherein at least two of the treatment electrodes are provided for iontophoretic purposes at the support and contact area for the tissue area to be treated.

13. The device according to claim 1, including a pH-sensor (9) for determining acidification in an immediate vicinity of the tumor cells, the pH-sensor being based on a semiconductor or on a conductance and impedance measurement.

14. The device according to claim 13, wherein the pH sensor (9) comprises at least one ion-selective field effect transistor (IS-FET).

15. The device according to claim 13, further comprising at least one additional sensor which is an ion or molecular sensor.

16. The device according to claim 12, wherein within the support and contact area for the area of tissue to be treated on a circumferential area of the porous membrane (7), several of the sensors (9) are arranged spaced apart from each other.

17. The device according to claim 1, wherein the active agent supply container (4) is formed by an outer chip (14), an adjacent chip (15) having the heating resistor, and a spacer (17, 23) which encloses a container space and seals it off.

18. The device according to claim 17, wherein the spacer comprises a sealing ring (17) in a form of an O-ring.

19. The device according to claim 17, wherein one of the two adjacent chips has on its side facing the other chip a ring wall (23) constructed by etching, and a front side of the ring wall is sealingly connected with the other chip and bonded by eutectic bonding.

20. The device according to claim 17, wherein the spacer (17, 23) is spaced from an outer edge area of the two adjacent chips and connection contacts (20) are arranged between the two chips in the outer edge area outside of the spacer.

21. The device according to claim 1, wherein the active agent supply container (4) has at least one capillary tube (19) for release of active agent.

* * * * *